US010974415B2

(12) United States Patent
Kuczmaszewski et al.

(10) Patent No.: US 10,974,415 B2
(45) Date of Patent: Apr. 13, 2021

(54) MACHINE FOR MOLDING COMPOSITE MATTER AND A METHOD OF PRODUCING CERAMICS-BASED COMPOSITE

(71) Applicant: MEDICAL INVENTI Spólka Akcyjna, Lublin (PL)

(72) Inventors: Józef Kuczmaszewski, Lublin (PL); Kamil Anasiewicz, Lublin (PL); Maciej Wlodarczyk, Biala (PL); Tomasz Warda, Lublin (PL); Anna Belcarz, Lublin (PL); Grażyna Ginalska, Lublin (PL)

(73) Assignee: MEDICAL INVENTI Spólka Akcyjna, Lublin (PL)

( * ) Notice: Subject to any disclaimer, the term of this patent is extended or adjusted under 35 U.S.C. 154(b) by 0 days.

(21) Appl. No.: 16/393,566

(22) Filed: Apr. 24, 2019

(65) Prior Publication Data
US 2020/0171702 A1   Jun. 4, 2020

(30) Foreign Application Priority Data
Dec. 4, 2018   (PL) .......................................... 428052

(51) Int. Cl.
*B28B 13/02*   (2006.01)
*C04B 35/622*   (2006.01)
(Continued)

(52) U.S. Cl.
CPC ............ *B28B 13/022* (2013.01); *A61C 13/20* (2013.01); *A61F 2/28* (2013.01); *B28B 3/028* (2013.01);
(Continued)

(58) Field of Classification Search
None
See application file for complete search history.

(56) References Cited

U.S. PATENT DOCUMENTS 4,053,268 A * 10/1977 Kishino .................... B28B 3/08
425/84
8,182,739 B2 * 5/2012 Okano ...................... B22F 3/10
419/6
(Continued)

FOREIGN PATENT DOCUMENTS

DE   2 238 265 A1   2/1974
PL   212866 B1   12/2012
WO   WO-2010123389 A2 *   10/2010   ............. A61L 27/46

*Primary Examiner* — Jacob T Minskey
*Assistant Examiner* — Baileigh Kate Darnell
(74) *Attorney, Agent, or Firm* — Myers Wolin, LLC

(57) ABSTRACT

The proposed solution solves a problem of designing a machine for producing molded composite parts that are homogeneously structured and the problem of finding a method for producing composite for implants. The essence of the design of the machine consists in that it has a portioning assembly, whereby above a mold form unit (14) there is a guiding unit (11) located opposite a dosing unit (6) and above the aforementioned guiding unit (11) there is a pressing assembly (20) slidingly mounted on a vertical frame (19) and which is equipped with at least one piston rod (25) with a rammer (27) at its end.
A preliminary molding is being performed by thoroughly filling a preform trough and then the matter is being pushed out of the preform trough in portions and then each portion is rammed separately until consistency containing less than 15% air is achieved.

4 Claims, 5 Drawing Sheets

Figure 1:
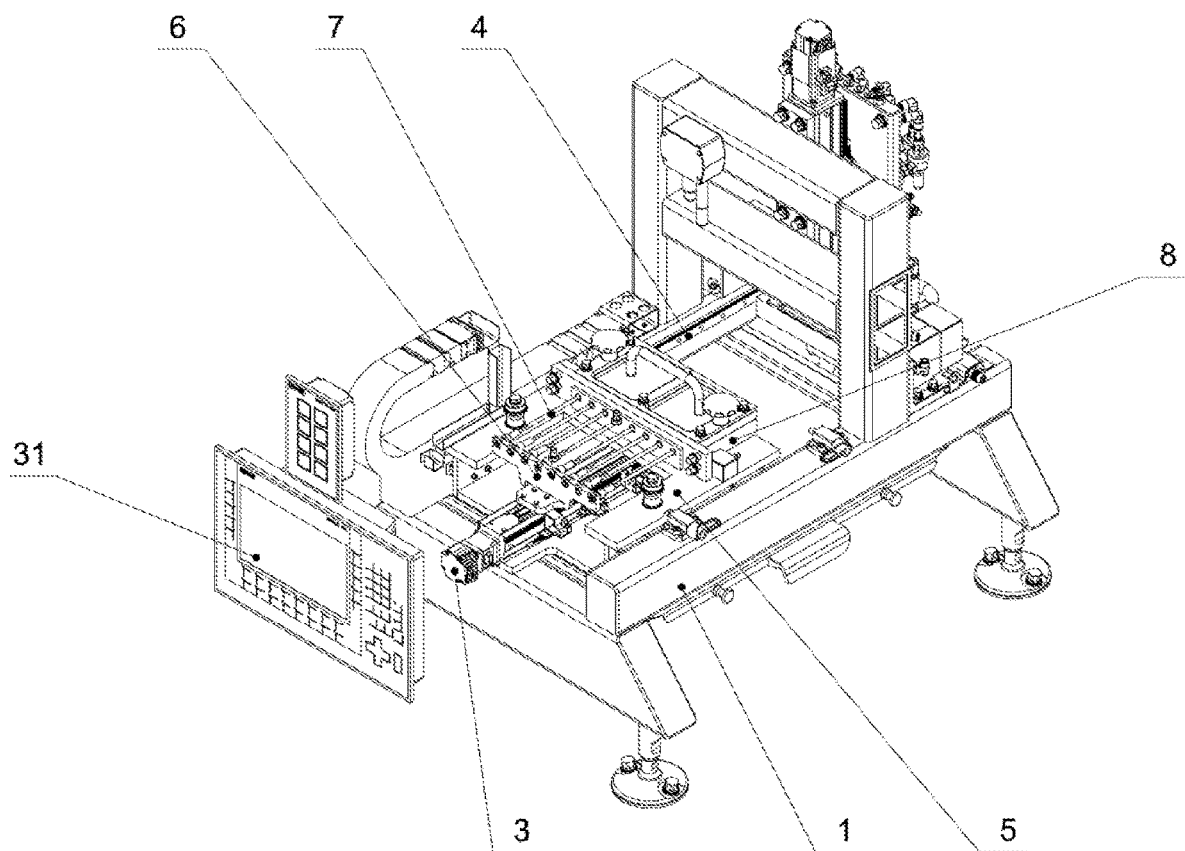

(51) Int. Cl.
    *B28B 17/00*     (2006.01)
    *A61C 13/20*     (2006.01)
    *A61F 2/28*     (2006.01)
    *B28B 3/02*     (2006.01)
    *B28B 3/06*     (2006.01)

(52) U.S. Cl.
    CPC ...... *B28B 3/06* (2013.01); *A61F 2310/00293* (2013.01)

(56) References Cited

U.S. PATENT DOCUMENTS

| | | | | |
|---|---|---|---|---|
| 2002/0114938 A1* | 8/2002 | Matsumoto | ............. | C04B 38/10 428/307.3 |
| 2005/0098915 A1* | 5/2005 | Long | ................... | B29C 43/003 264/109 |
| 2008/0260565 A1* | 10/2008 | Okano | ................... | C22C 29/12 419/32 |
| 2009/0215009 A1* | 8/2009 | Noishiki | ................ | A61L 27/12 433/215 |

* cited by examiner

MACHINE FOR MOLDING COMPOSITE MATTER AND A METHOD OF PRODUCING CERAMICS-BASED COMPOSITE

This nonprovisional patent application is being filed under 35 U.S.C. 111(a) and claims a priority from the Polish Patent Application No. P.428052, filed on Dec. 4, 2018, the content of which is incorporated by reference herein.

The solution relates to a machine for molding composite blocks and to a method of producing composite based on ceramics, especially HAp, for implants.

Ceramic granules from hydroxyapatite HAp or from tricalcium phosphate TCP are used as materials for implants but due to their fragility and poor plasticity their application in surgery, especially oral and facial, is limited.

From patent description DE2238265 there is known a press having independently adjustable stages for manufacturing a multi-layered laminated product from powdered materials. The number of these stages depends on the number of powdered materials used. Each stage includes a piston whose stroke is guided by and limited by a cylindrical portion of an adjacent piston placed below the first one. The punch is hydraulically driven and its position is adjustable. The press is equipped with a feeder.

There are known methods of making the above mentioned ceramic materials more malleable by using water suspension of curdlan heated to 40° C.

From Polish patent PL 212866 there is known a method of producing bio-active composite based on calcium-phosphate bio-ceramics in the form of granules and which is mixed with curdlan in proportions according to a specific formula and then the mixture is heated in temperatures of 80-100° C.

The object of the solution is a machine for molding and ramming malleable matter and a method of producing ceramics-based composite characterized by high mechanical endurance.

Unexpectedly, it turned out that reducing presence of air within composite structures to a minimum significantly improves their endurance.

According to the present patent application the forming machine is characterized in that it has a portioning assembly which comprises a dosing unit, favorably equipped with at least one linearly driven push rod, and a preliminary molding unit, favorably equipped with at least one trough, whereby both these units are slidingly mounted on a plate of a carriage which is connected with linear drive. Above a mold form unit there is a guiding unit placed opposite a dosing unit. Above the guiding unit there is a pressing assembly slidingly mounted on a vertical frame. The pressing assembly is equipped with at least one piston rod having at its end a rammer. The piston rod is placed within a casing into which pneumatic pipes are connected. The portioning assembly is slidingly mounted parallely relative to the guiding unit. Drives of all the operating assemblies are connected with a control unit. The numbers of piston rods and of troughs are related to the number of the rammers and molds.

Favorably, the rammer, which is cylindrically shaped, in its middle part has a narrowing, and on its side rings there are shallow furrows situated along the axis of the rammer.

Favorably, the mold form unit is mounted by means of clamps and thus can be easily dismantled.

The machine guarantees that the matter for the composite is properly compacted. The efficient removal of the air from the matter is assured thanks to the design of the rammer, which allows air bubbles to move between the rammer and the mold. Multiple pressing devices and multiple mold forms accelerate the process of producing semi-finished products. Automated control ensures reproducible manufacture.

An example of the object of the solution is presented on diagrams, whereby

Figure 2:
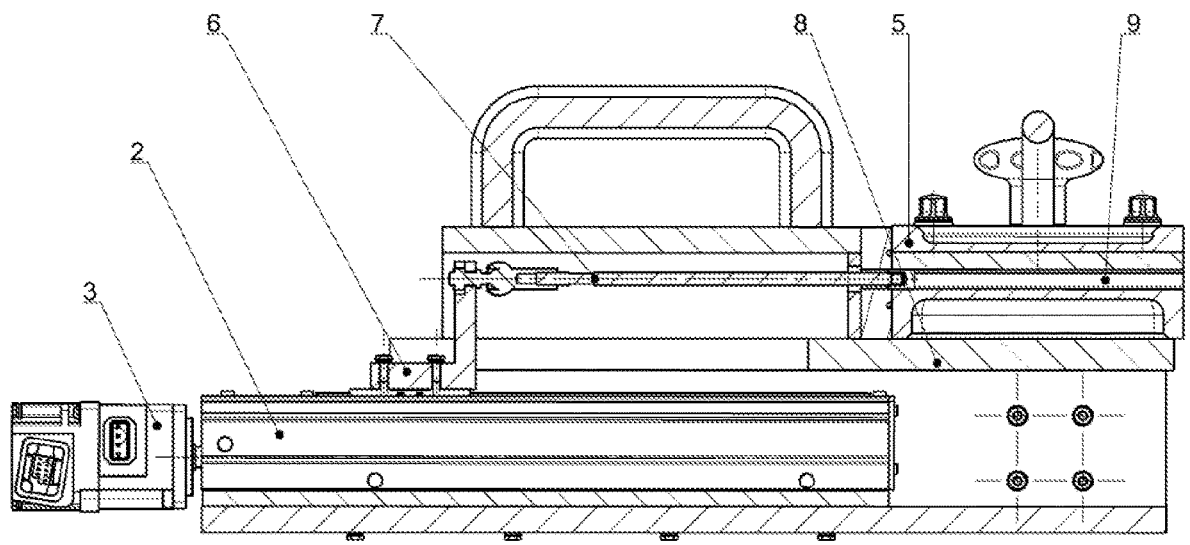
Figure 3:
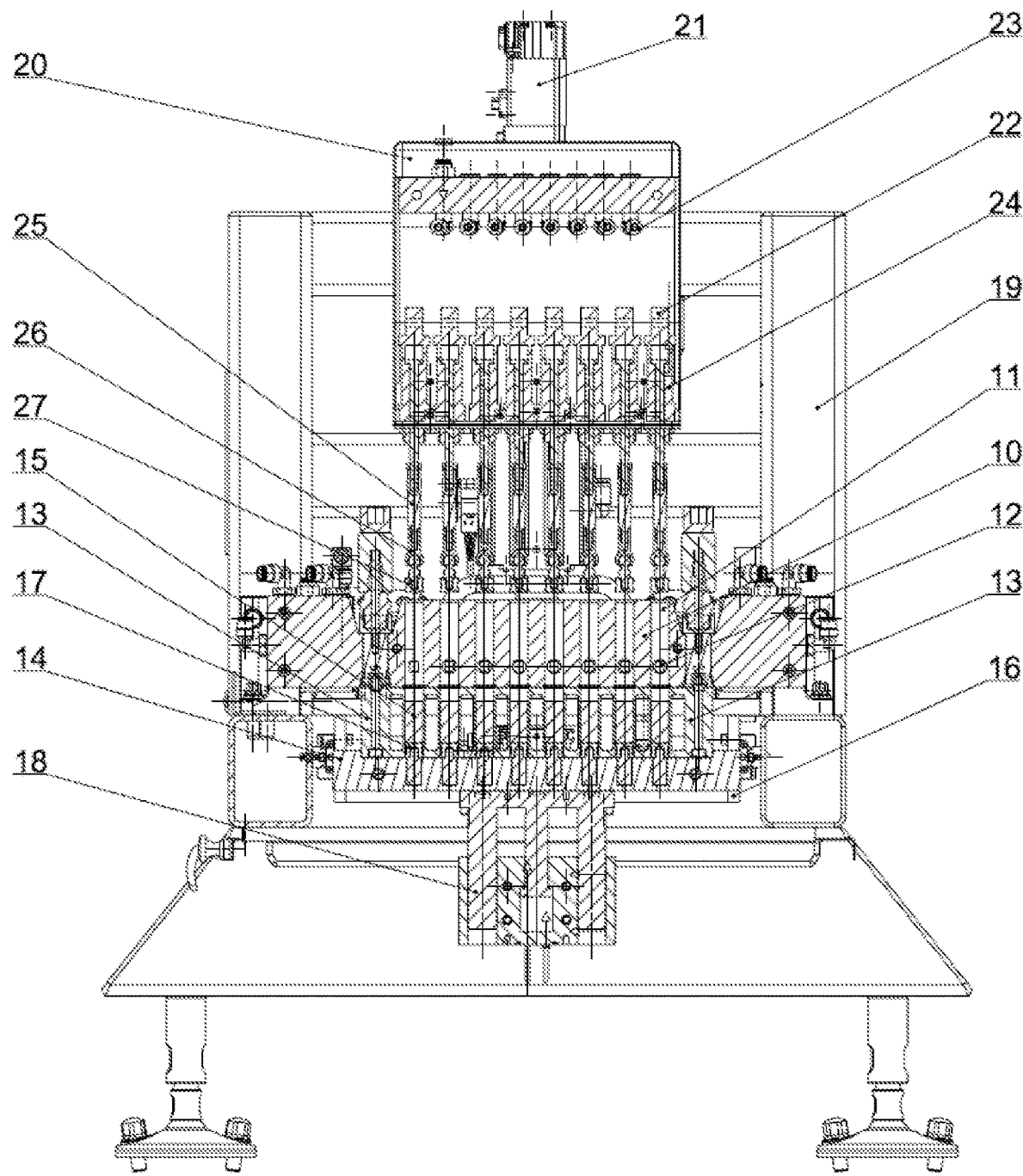
Figure 4:
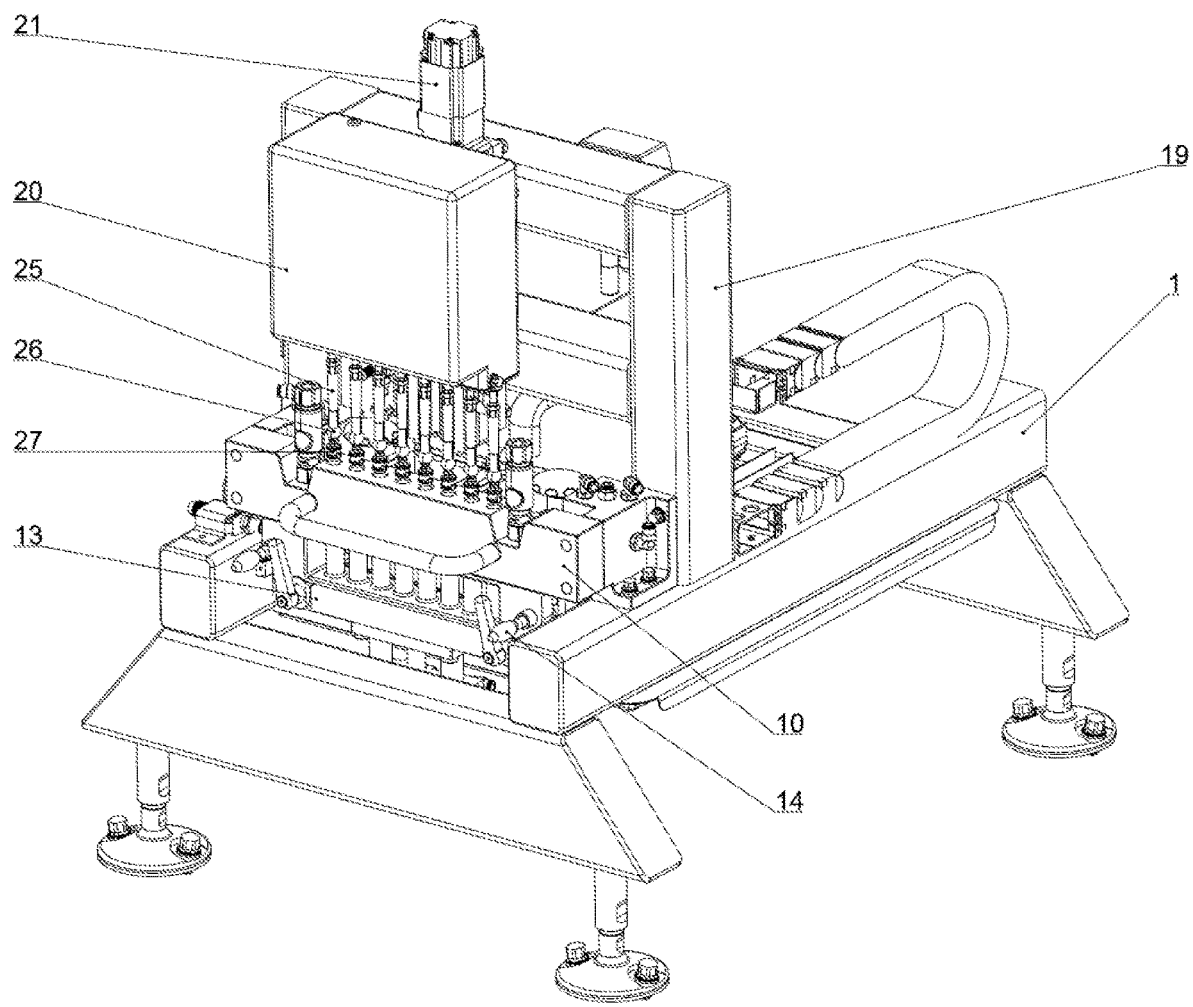
Figure 5:
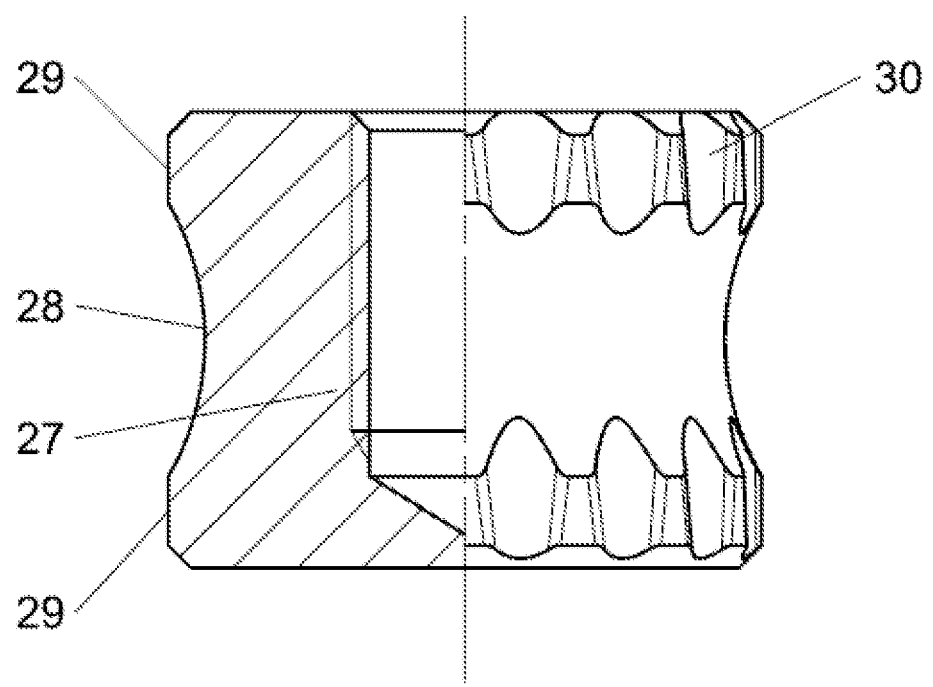
Figure 6:
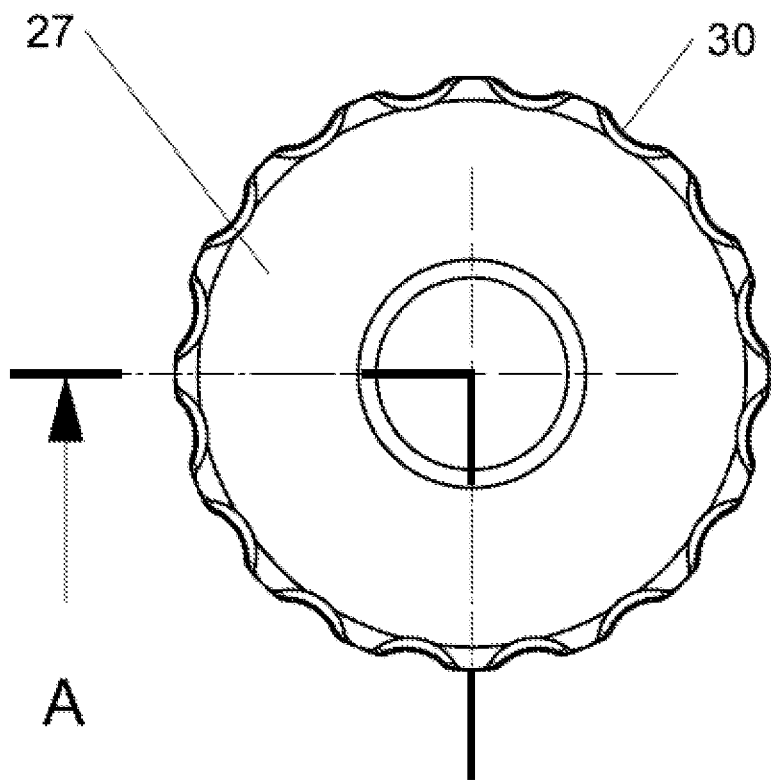

FIG. 1 presents axonometric drawing of the molding machine viewed from the carriage side, FIG. 2 side-view of the plate of the carriage together with the dosing assemblies, FIG. 3 longitudinal sectional view along axis of piston rods, FIG. 4 axonometric drawing of the machine viewed from the pressing assembly side, FIG. 5 the rammer with partial section along line A, and FIG. 6 the rammer front view.

A molding machine having a bed 1 upon which a carriage 2 with a linear drive 3 on guides 4 is slidingly mounted. A dosing unit 6 with eight push rods 7 and a preliminary molding unit 8, which has eight troughs 9 running along axis of the push rods 7, are both screwed onto a plate 5 of the carriage 2. The preliminary molding unit 8 is exchangeable and is mounted on the plate 5 of the carriage 2 using centering pins. The carriage 2 is connected with a primary linear drive 10. On the bed 1 there is a guiding unit 11 installed having eight through-holes 12 situated vertically, and eight cylindrical horizontal holes 13 which are situated along the guiding unit 11 starting from its front wall, which is located at the side of the preliminary molding unit, up to the through-holes 12. The axis of the horizontal holes 13 flush with the axis of the push rods 7. Under the guiding unit 11 there is a mold form unit 14 slidingly mounted and attached onto a frame 19 with clamps which make it easy to dismantle. The mold form unit 14 has eight cylindrical mold forms 15 whose axis flush with the axis of the through-holes 12. Under the mold form unit 14 there is a slat 16 which has eight plugs 17 and which is supported by a pneumatic actuator 18.

Mounted on the bed 1 there is the frame 19 onto which the pressing unit 20, coupled with the secondary linear drive 21, is fitted. The pressing unit 20 is equipped with eight pressing mechanisms 22. The pressing mechanism 22 consists of a casing 24 into which two pneumatic pipes 23 are connected. In the casing 24 there is a piston rod 25 connected via a joint 26 and via a screw joint with a rammer 27. The rammer 27 has a cylindrical shape with a narrowing 28 which creates two rings 29 on the sides. On the cylindrical surface of the rings 29 of the rammer 27 there are shallow furrows 30 having a minimal clearance relative to a diameter of a mold and situated along the axis of the rammer 27. All the drives of the operating assemblies are connected with a control unit 31.

All the elements of the assemblies that might get soiled, especially the preliminary molding unit 8, the push rods 7, the mold form unit 14, and the guiding unit 11, can be easily dismantled for cleaning. The mold form unit 14 is made of chemically resistant material.

The machine functions as follows: The preliminary molding unit 8, with the troughs 9 thoroughly filled, is placed on the plate 5 of the carriage 2 and positioned with precision. On the front side, after lifting the pressing unit 20, the mold form unit 14 is placed. The pneumatic actuator 18 supports the slat 16 with the plugs 17 which seal individual forming chambers 15. After the pressing unit 20 is lowered, a pre-programmed process of ramming is initiated running in cycles consisting of a feeding movement of the push rods 7, which supply portions of composite to the through-holes 12 of the guiding unit 11, and a synchronized with it movement of the rammers 27. The rammers 27 and the push rods 7 move alternately and perpendicularly in relation to each other within the guiding unit 11. When a portion of a composite is placed in the through-holes 12 the ramming is being executed by the rammer 27 moving three times. The cycle of ramming each individual portion of a composite is repeated 10-13 times. After the composite matter has been rammed, the pressing unit 20 is moved to the back and the mold form unit 14 is dismantled and then inlets of the mold forms 15 are plugged and next moved for a heat treatment.

The solution also relates to a method of producing ceramics-based calcium phosphate composite.

According to the solution a method for producing ceramics-based calcium phosphate composite is characterized in that into a water suspension, which contains 76-175 grams of β-1.3-glucan (hereinafter referred to as curdlan) per 1 liter of water, calcium phosphate ceramics in the form of porous granules with a total weight of 300-800 g, favorably from 415 to 800 g, is added and mixed until an optimum homogeneity is achieved and then preliminary molding takes place whereby a preform trough is thoroughly filled with the matter and then the matter is pushed into a mold where each portion is rammed separately until consistency containing less than 15% air is achieved and, after accurate ramming, it undergoes 5-120 minutes of heat treatment in temperatures between 80-100° C., and after that a finished product is removed from the mold.

Favorably, the granules have sizes from 0.1 to 0.9 mm and an open porosity from 50% to 70%. The most favorable porosity is between 60 and 70%.

Favorably, prior the heat treatment, the mold containing the rammed matter is sealed with a plug or, otherwise, the air exposure of the rammed matter is restricted by using other means.

EXAMPLES

Example I 170 g of β-1.3-glucan was mixed with 1.000 ml of water and then 350 g of calcium phosphate ceramics HAp granules with a diameter of 0.3-0.4 mm were added and the ingredients were mixed until homogeneous consistency has been achieved. From the resulting matter a sample having about 6.5 cm$^3$ in volume was taken and the preform trough with a capacity of 5550 mm$^3$ was thoroughly filled with it. The remaining excess of the matter was removed. In the next step portions of the matter having a volume of about 0.4 cm$^3$ were being fed successively from the trough into a mold having a diameter of 13 mm and each portion was rammed three times with a force of 15 N. The obtained semi-finished product having a volume of 4 cm$^3$ was heat-treated for 25 minutes at 98° C. and after that cooled to room temperature and then removed from the mold. It has been concluded that the homogeneous composite thus obtained had low plasticity and during a compression test the sample sustained deformation of 18% prior its destruction.

The composite has been dried for 12 hours at 40° C. The overall volume of pores (air content) in the dried sample of the composite, as measured with a method of computed micro tomography (with threshold value for pores detection of 15 μm), amounted to 6.74%±1.15%. More than 90% of all pores in the sample were of the closed type.

Example II

For testing purpose 40 g of β-1.3-glucan mixed with 500 ml of water was used. 225 g of calcium-phosphate ceramics TCP granules with diameters of between 0.4-0.6 mm was added to the water suspension and then the components have been mixed until homogeneous matter was obtained.

From the obtained matter a sample having about 10 cm$^3$ in volume was taken and put into the preform trough with a capacity of 8.350 mm$^3$ which was thoroughly filled and the remaining excess of the matter was removed. In the next step portions of the matter having a volume of about 750 mm$^3$ each were being pushed out the trough into a mold with a diameter of 15 mm where each portion has been rammed three times with a force of 20 N. The obtained product having a volume of 7 cm$^3$ was heat-treated for 20 minutes at 93° C. The finished product, after having been cooled and after removing it from the mold, was examined under a microscope and no empty spaces resulting from the air remaining in the semi-finished product undergoing the molding process have been discovered during this examination.

The overall volume of pores (air content) in the dried sample of the composite, as measured with a method of computed micro tomography (with threshold value for pores detection of 15 μm), amounted to 7.24%±1.11%. About 30% of those pores have diameters between 45-75 μm. No pores with a diameter more than 0.3 mm had been detected, which indicates highly homogeneous structure of the product and high efficiency of the molding process performed by the machine hereby described.

The invention claimed is:

1. A method of producing composite based on calcium phosphate ceramics mixed with curdlan, wherein
    into a water suspension containing 76-175 grams of β-1,3-glucan, hereinafter referred to as curdlan, per one litre of water calcium phosphate ceramics in the form of porous granules weighing from 415 to 800 g, are added and mixed until a composite matter having homogeneous consistency has been achieved and then preliminary moulding takes place wherein
    a preform trough is manually precisely filled with a matter which is pushed by a force generated by push rods (7) of a dosing unit (6) moved by a linear drive (3) into a detachable mould wherein
    a portioning assembly comprises a dosing unit, equipped with at least one linearly driven push rod, and an exchangeable preliminary molding unit, equipped with at least one trough, are slidingly mounted on a plate of a carriage which is connected to linear drive (3), wherein
    each portion of the matter is rammed separately 10-13 times until consistency containing less than 15% of air is achieved and, after ramming, the matter together with the detachable mould is being kept for 5-120 minutes in temperatures between 80-100° C., and after that a finished composite product is removed from the detachable mould.

2. The method in accordance with claim 1, wherein the porous granules have a diameter of between 0.1 to 0.9 mm and an open porosity ratio of between 50% and 70%.

3. The method in accordance with claim 2, wherein the open porosity ratio of the porous granules is between 60% and 70%.

4. The method in accordance with claim 1, wherein the mould containing a rammed matter containing less than 15% of air, prior to heat treatment, is plugged or, alternatively, a contact of the rammed matter with an air is restricted.

* * * * *